(12) United States Patent
Gao et al.

(10) Patent No.: US 10,099,005 B2
(45) Date of Patent: Oct. 16, 2018

(54) DRIVE MECHANISM

(71) Applicant: Johnson Electric S.A., Murten (CH)

(72) Inventors: Jian Dong Gao, Shenzhen (CN); Wai To Li, Hong Kong (CN)

(73) Assignee: JOHNSON ELECTRIC S.A., Murten (CH)

( * ) Notice: Subject to any disclaimer, the term of this patent is extended or adjusted under 35 U.S.C. 154(b) by 240 days.

(21) Appl. No.: 14/921,697

(22) Filed: Oct. 23, 2015

(65) Prior Publication Data

US 2016/0114098 A1 Apr. 28, 2016

(30) Foreign Application Priority Data

Oct. 24, 2014 (CN) .......................... 2014 1 0583656

(51) Int. Cl.
| | | |
|---|---|---|
| A61M 31/00 | (2006.01) | |
| A61M 5/142 | (2006.01) | |
| H02K 7/116 | (2006.01) | |
| H02K 7/14 | (2006.01) | |
| H02K 11/21 | (2016.01) | |
| A61M 5/168 | (2006.01) | |
| F16H 25/20 | (2006.01) | |
| H02K 7/06 | (2006.01) | |
| A61M 5/14 | (2006.01) | |

(52) U.S. Cl.
CPC ........ *A61M 5/142* (2013.01); *A61M 5/16831* (2013.01); *F16H 25/20* (2013.01); *F16H 25/2015* (2013.01); *H02K 7/116* (2013.01); *H02K 7/14* (2013.01); *H02K 11/21* (2016.01); *A61M 5/14* (2013.01); *F16H 2025/204* (2013.01); *F16H 2025/2031* (2013.01); *F16H 2025/2081* (2013.01); *H02K 7/06* (2013.01)

(58) Field of Classification Search
CPC ...... F16H 2025/204; F16H 2025/2081; A61M 5/142; A61M 5/16831
See application file for complete search history.

(56) References Cited

U.S. PATENT DOCUMENTS

| | | | |
|---|---|---|---|
| 8,035,371 B2 | 10/2011 | Budde et al. | |
| 8,343,099 B2 | 1/2013 | Peter et al. | |
| 2003/0009133 A1* | 1/2003 | Ramey | A61M 5/1456 604/155 |
| 2008/0077081 A1* | 3/2008 | Mounce | A61M 5/1413 604/67 |
| 2013/0281965 A1* | 10/2013 | Kamen | A61M 5/172 604/500 |

* cited by examiner

*Primary Examiner* — Kevin C Sirmons
*Assistant Examiner* — Tiffany Legette-Thompson
(74) *Attorney, Agent, or Firm* — Muncy, Geissler, Olds & Lowe, P.C.

(57) ABSTRACT

A drive mechanism for a medication delivery device includes a motor, a housing, a gear cover, a gear transmission system, a helical transmission system, and a sensor system. The helical transmission system includes a plug, a screw shaft, and a sliding block connecting the plug to the screw shaft. The gear transmission system includes a first gear disposed on an output shaft of the motor and a second gear disposed on one end of the screw shaft. Dual gears interconnect the first and second gears. The motor drives the plug along a linear path by rotating the screw shaft via the gear transmission system, causing the sliding block to move along the screw shaft. The sensor system monitors the driving process. The plug provides the force required to effect the dosing of the medication.

14 Claims, 10 Drawing Sheets

DRIVE MECHANISM

CROSS REFERENCE TO RELATED APPLICATIONS

This non-provisional patent application claims priority under 35 U.S.C. § 119(a) from Patent Application No. 201410583656.0 filed in The People's Republic of China on Oct. 24, 2014, the entire contents of which are hereby incorporated by reference.

FIELD OF THE INVENTION

This invention relates to medication delivery devices and in particular, to a drive mechanism for a medication delivery device, especially an insulin pump.

BACKGROUND OF THE INVENTION

Today diabetes has become the fourth leading cause of death after cardiovascular disease, cerebrovascular disease and cancer. For diabetes patients, the most effective method is to inject insulin over a long period of time.

Currently there are various types of long term quantitative insulin syringes and insulin pumps. Insulin pump therapy is an insulin treatment method which involves the use of an artificial intelligent controlled insulin input device which simulates the physiological secretions of insulin patterns by means of continuous subcutaneous insulin infusion so as to control blood sugar level. The use of insulin pumps has more than 20 years of history at the international level. Findings of diabetes control and complications trial (DCCT) establish an important position for intensifying insulin therapy in diabetes treatment and complication control, and it also provides high quality clinical evidence for clinical application of insulin pumps. The study confirmed that, in comparison with multiple insulin injections, insulin pump can more effectively control the glycosylated hemoglobin (HbA 1c) level, while also improving the quality of lives of patients. Since the DCCT study results were published, the number of insulin pumps used by diabetes patients in the United States has increased remarkably. In 2005, the number of insulin pump users in the United States has reached 278,000.

However, the drive mechanism for the conventional insulin injection often has insufficient pressure, low dosing precision, potential safety concerns, high noise level and high power consumption. In addition, the conventional drive mechanism usually has a large size, making it inconvenient to use during the treatment process.

SUMMARY OF THE INVENTION

Hence, there is a desire for a drive mechanism for a medication delivery device which is capable of precise dosing of various viscous medications. Optionally, the drive mechanism has a compact construction, low noise and low power consumption and the driving process can be monitored via a sensor system.

Accordingly, in one aspect thereof, the present invention provides a drive mechanism for a medication delivery device, comprising a motor, a housing, a gear cover connected to the housing, a gear transmission system disposed in a space defined by the housing and the gear cover, a helical transmission system disposed in an interior of the housing and connected to the motor by the gear transmission system, and a sensor system. The helical transmission system comprises a plug, a screw shaft disposed in an interior of the plug, and a sliding block threadingly connected with the screw shaft. The sliding block is attached to or integrally formed with the plug. The motor is configured to rotate the screw shaft of the helical transmission system via the gear transmission system, to thereby move the plug along a linear path relative to the housing. The sensor system is configured to monitor operation of the drive mechanism.

Preferably, a plurality of gear shafts parallel to an output shaft of the motor is disposed in the housing, the gear transmission system comprises a first gear disposed on the output shaft of the motor, a plurality of dual gears respectively disposed on the plurality of gear shafts, and a second gear disposed on one end of the screw shaft adjacent the gear cover; the first gear meshes with a first dual gear of the plurality of dual gears adjacent the first gear, the dual gears mesh with one another, the last one of the plurality of dual gears adjacent the second gear meshes with the second gear.

Preferably, the housing comprises a first receiving portion for receiving the gear transmission system, and a second receiving portion, perpendicular to the first receiving portion, for receiving the plug; the first receiving portion defines an opening at a side remote from the second receiving portion and has an internal space in communication with an internal space of the second receiving portion; the gear cover is mounted to the first receiving portion.

Preferably, a connecting portion is formed at an end of each of the first receiving portion and the second receiving portion.

Preferably, a first through hole is defined in an outer surface of the first receiving portion at a location adjacent the second receiving portion, the motor is perpendicularly disposed on the outer surface of the first receiving portion, with its output shaft passing through the first through hole, the gear transmission system is disposed within the first receiving portion and the gear cover, and the helical transmission system is disposed within the second receiving portion.

Preferably, each of the dual gears comprises a first meshing portion with a smaller diameter and a second meshing portion with a greater diameter, the first gear meshes with the second meshing portion of a first dual gear of the dual gears, the first meshing portion of the first dual gear meshes with the second meshing portion of a next stage dual gear that is immediately next to the first dual gear, the first meshing portion of the next stage dual gear meshes with the second meshing portion of a further next stage dual gear that is immediately next to the next stage dual gear, and the first meshing portion of the last stage dual gear meshes with the second gear.

Preferably, a ball bearing is disposed at a side of the second gear adjacent the gear cover, a first collar is disposed between the ball bearing and the second gear, an annular baffle plate is disposed at a side of the second gear remote from the gear cover, the baffle plate is mounted to an inner surface of the first receiving portion of the housing, and the baffle plate is coaxial with the second gear.

Preferably, a plurality of protrusions is formed on an inner circumferential surface of one end of the second receiving portion remote from the first receiving portion of the housing, and the protrusions contact an outer surface of the plug.

Preferably, a second through hole is formed in a face of the gear cover at a location corresponding to the screw shaft, a recess is formed in a side of the gear cover adjacent the second through hole, a groove is formed in an outer surface of the face of the gear cover, the groove extends through two opposite end surfaces of the gear cover, and an annular connecting portion is perpendicularly disposed within the groove.

Preferably, the sensor system comprises a linear sensor disposed in the helical transmission system and a rotation sensor disposed in the gear transmission system or adjacent the output shaft of the motor.

Preferably, an encoder disc is disposed on the output shaft of the motor adjacent an inner side of the first gear, the encoder disc is mounted to the output shaft via a second collar, the rotation sensor is mounted to the interior of the housing and disposed over the encoder disc, and the linear sensor is disposed on an outer surface of the plug.

Preferably, a flexible circuit board is disposed on the outer surface of the housing, the flexible circuit board includes a flexible circuit board main body, a first extension portion and a second extension portion; the first extension portion lays on the outer surface of the second receiving portion of the housing and is electrically connected to the linear sensor, the second extension portion is attached to an end face of the motor and is electrically connected to the rotation sensor, the flexible circuit board is electrically connected to a controller.

Preferably, a guiding portion is formed on one of the second receiving portion of the housing and the plug, a guiding slot is formed in the other of the second receiving portion of the housing and the plug, and the guiding portion is movable in the guiding slot to guide movement of the plug.

Preferably, a blocking portion is formed at an end of the guiding slot to limit outward movement of the plug.

Preferably, the motor is a stepping motor, the sensor system comprises a reset-detecting sensor disposed in the helical transmission system and a rotation sensor disposed in the gear transmission system or adjacent the output shaft of the motor.

Preferably, a stop is provided to limit over-retraction of the plug into the housing.

BRIEF DESCRIPTION OF THE DRAWINGS

A preferred embodiment of the invention will now be described, by way of example only, with reference to figures of the accompanying drawings. In the figures, identical structures, elements or parts that appear in more than one figure are generally labeled with a same reference numeral in all the figures in which they appear. Dimensions of components and features shown in the figures are generally chosen for convenience and clarity of presentation and are not necessarily shown to scale. The figures are listed below.

DETAILED DESCRIPTION OF THE PREFERRED EMBODIMENTS

Figure 1:
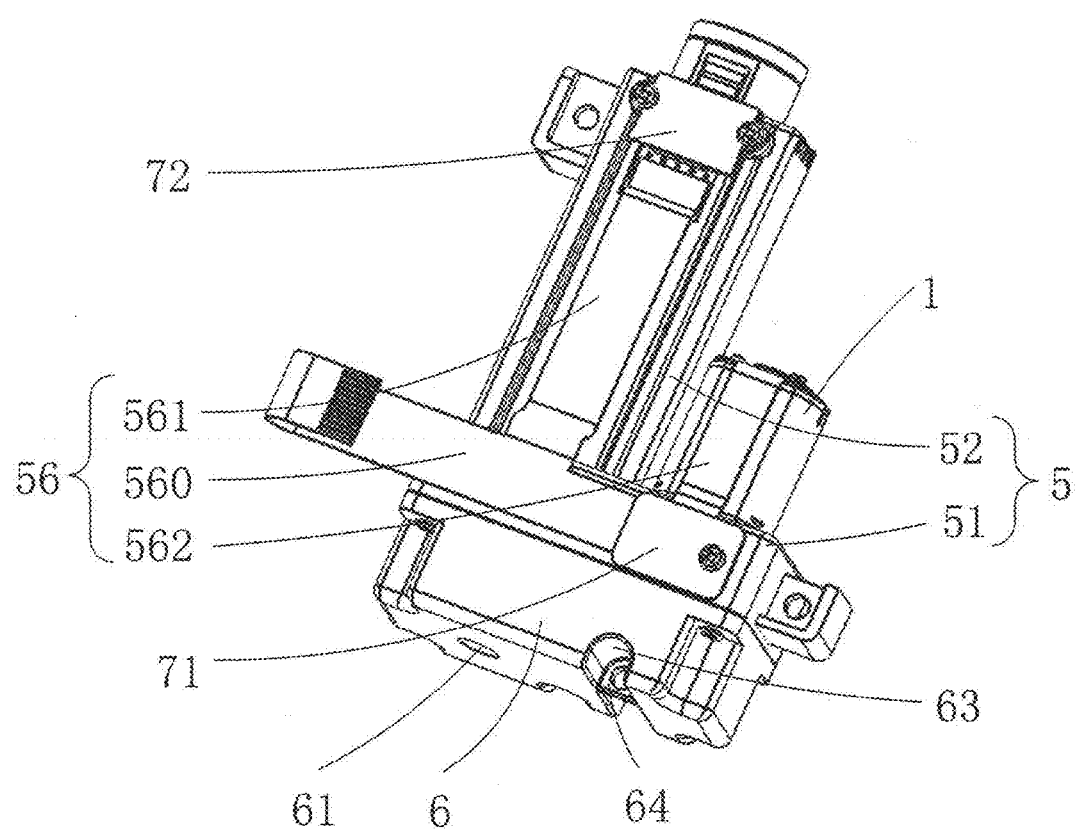
FIG. 1 is a perspective view of a drive mechanism for a medication delivery device according to one embodiment of the present invention.
Figure 2:
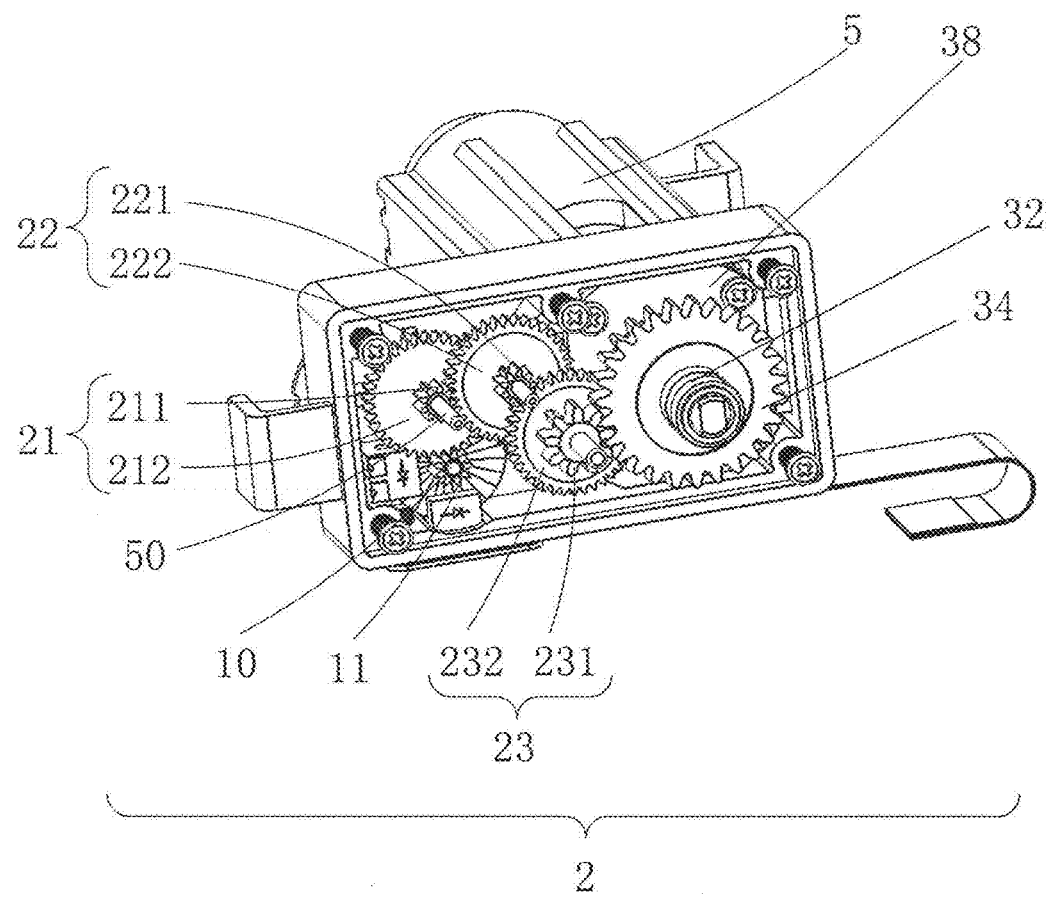
FIG. 2 illustrates a gear transmission system of the drive mechanism of FIG. 1.
Figure 3:
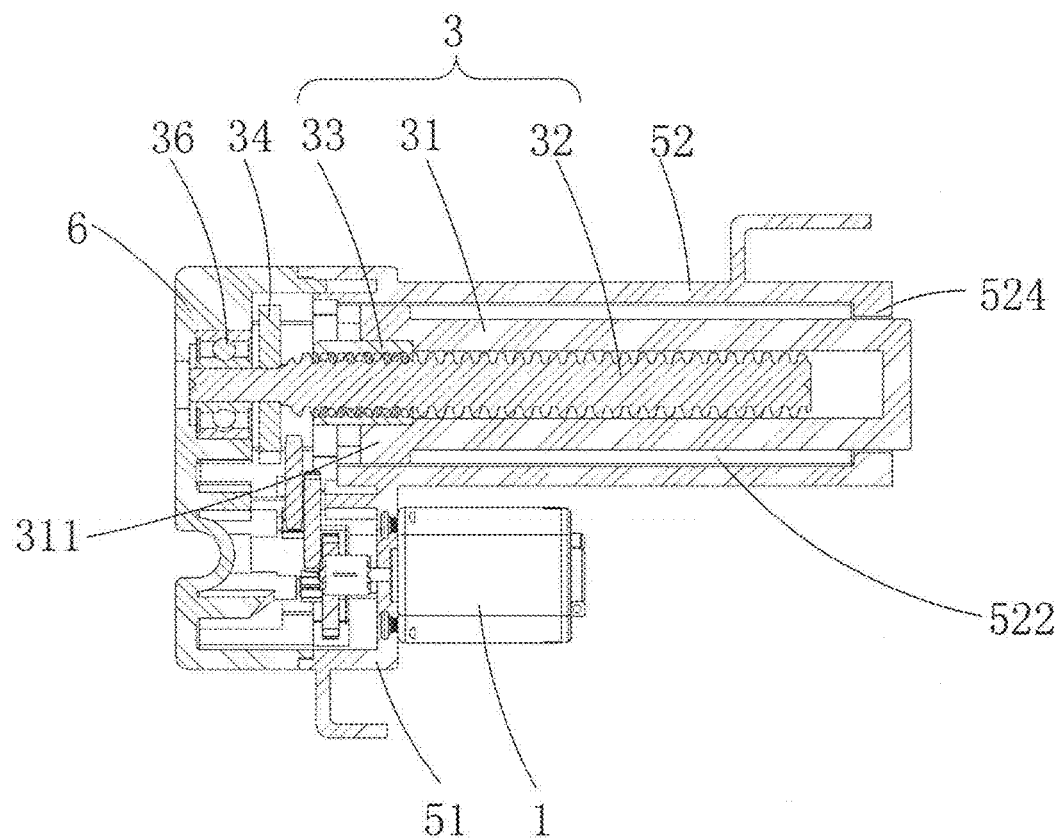
FIG. 3 is a sectional view of the drive mechanism of FIG. 1.
Figure 4:
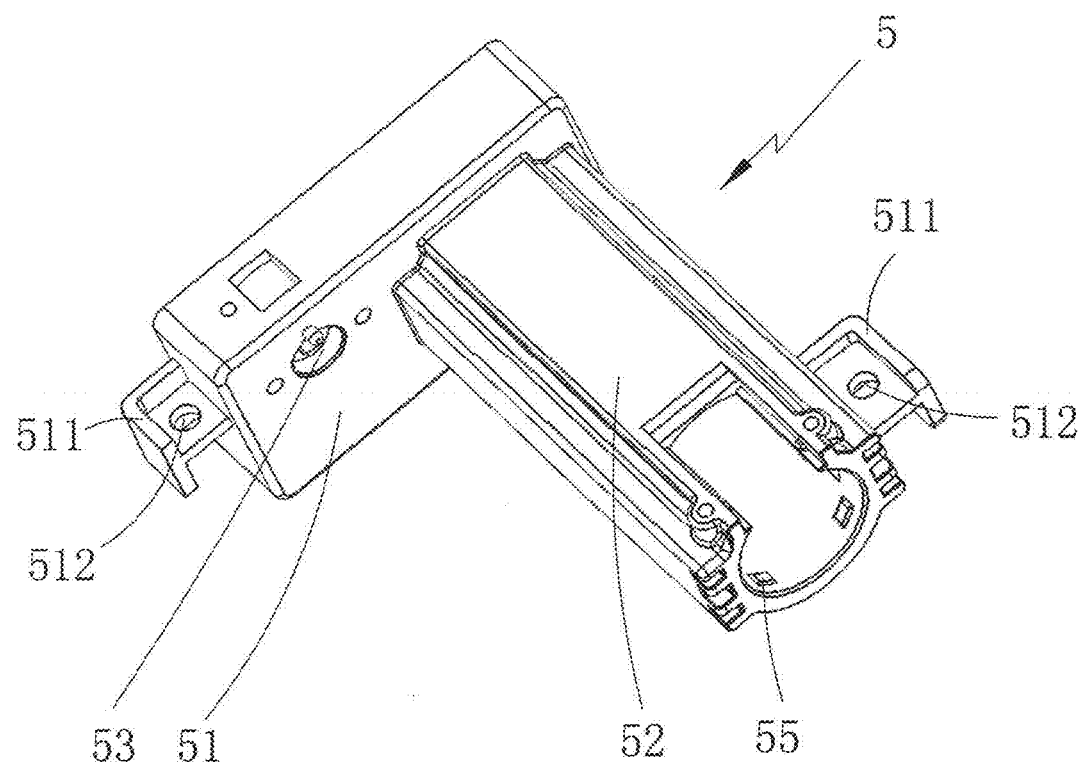
FIG. 4 illustrates a housing of the drive mechanism of FIG. 1.
Figure 5:
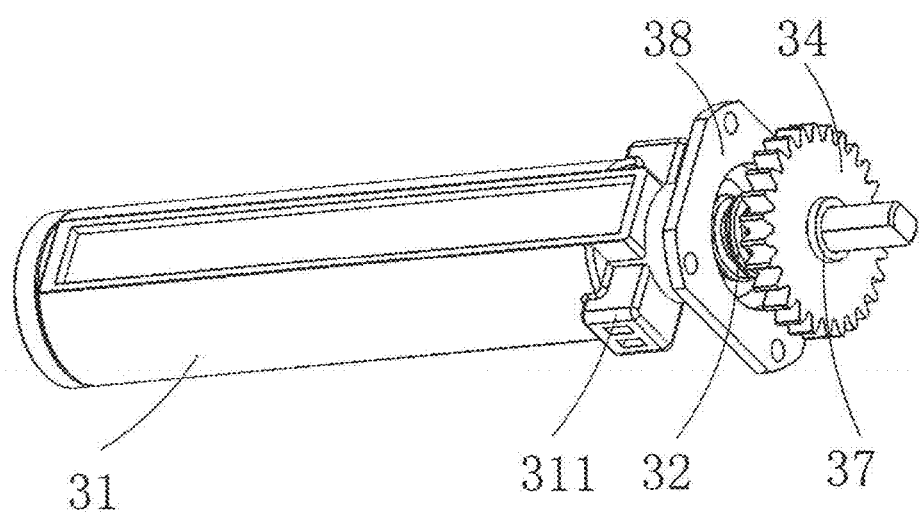
FIG. 5 illustrates a helical transmission system of the drive mechanism of FIG. 1.

Referring to FIGS. 1 to 11, a drive mechanism for a medication delivery device in accordance with one embodiment of the present invention includes a motor 1, a housing 5, a gear cover 6 connected to the housing 5, a gear transmission system 2 disposed within the housing 5 and the gear cover 6 and connected with the motor 1, a helical transmission system 3 disposed within the housing 5 and connected with the gear transmission system 2, and a sensor system 4.

The helical transmission system 3 includes a plug 31, a screw shaft 32 disposed in an interior of the plug 31, a sliding block 33 attached around the screw shaft 32 and threadingly engaged with the screw shaft. The sliding block 33 may be directly or indirectly mounted to the plug 31 or alternatively formed as an integral part of the plug 31. For example, an inner surface of the plug 31 may be formed with a screw thread. In this embodiment, the sliding block 33 is a nut and positioned at a bottom of the plug 31 by interference fit or insert molding, such that, upon rotation of the screw shaft 32, the nut drives the plug 31 along a linear path into or out of a second receiving portion 52 of the housing 5.

A plurality of gear shafts 50 parallel to an output shaft 10 of the motor 1 is disposed in the housing 5. The gear transmission system 2 includes a first gear 11 mounted on the output shaft 10 of the motor 1, a plurality of dual gears respectively mounted on the gear shafts 50, and a second gear 34 mounted on the screw shaft 32 at an end thereof adjacent the gear cover 6. The screw shaft 32 rotates with the second gear 34.

In the preferred embodiment of FIG. 1, the motor 1 is preferably a permanent magnet direct current (PMDC) motor. The number of the gear shafts 50 and the number of the dual gears are both three. Each dual gear includes a first meshing portion with a smaller diameter and a second meshing portion with a larger diameter. The use of the dual gear formed by two gears with different diameters avoids the axis misalignment problem during assembly of ordinary gears.

Specifically, the first gear 11 meshes with the second meshing portion 212 of the first dual gear 21, the first meshing portion 211 of the first dual gear 21 meshes with the second meshing portion 222 of a next stage dual gear 22 that is immediately next to the first dual gear 21, the first meshing portion 221 of the next stage dual gear 22 meshes with the second meshing portion 232 of a further next stage dual gear 23 that is immediately next to the next stage dual gear 22, and the first meshing portion 231 of the dual gear 23 meshes with the second gear 34. The motor 1 drives the screw shaft 32 of the helical transmission system 3 via the gear transmission system 2, such that the plug 31 moves under the action of the sliding block 33 to provide controlled dosing of various viscous medications. With the sensor system 4 monitoring the driving process, dosing precision can be ensured.

The housing 5 includes a first receiving portion 51 for receiving the gear transmission system 2 and the second receiving portion 52 perpendicular to the first receiving portion 51 for receiving the plug 31. The first receiving portion 51 has an opening at a side away from the second receiving portion 52. The internal space of the second receiving space 52 communicates with the internal space of the first receiving portion 51. An outer surface of the first receiving portion 51 defines a first through hole 53 at a location adjacent the second receiving portion 52. The gear cover 6 is mounted to the open side of the first receiving portion 51 and covers the opening. A connecting portion 511 is disposed at an end of each of the first receiving portion 51 and the second receiving portion 52. A third through hole 512 is defined through each connecting portion 511. The connecting portions 511 are used to connect the drive mechanism to an external device.

The motor 1 is perpendicularly disposed on the outer surface of the first receiving portion 51, with its output shaft 10 passing through the first through hole 53. The gear transmission system 2 is disposed in the interior of the first receiving portion 51 and the gear cover 6. The helical transmission system 3 is disposed in the interior of the second receiving portion 52.

An end of the screw shaft 32 extending out of the second gear 34 is supported by a bearing 36. The bearing 36 is mounted in a bearing mounting hole of the gear cover 6. In the illustrated embodiment, the bearing mounting hole is a counter bore. The bearing 36 is preferably a ball bearing. A first collar 37 is disposed between the ball bearing 36 and the second gear 34 for axially positioning the ball bearing 36. The presence of the ball bearing 36 reduces the gap between the screw shaft 32 and the gear cover 6. An annular baffle plate 38 is disposed at a side of the second gear 34 remote from the gear cover 6. The baffle plate 38 is mounted to an inner surface of the first receiving portion 51 of the housing 51 with screws. The baffle plate 38 is coaxial with the second gear 34 and forms a stop to contact the plug 31 to define an innermost position of the plug 31 when the plug 31 retracts into the housing 5 (i.e. moves toward the gear cover 6). A plurality of protrusions 55 is formed on an inner circumferential surface of the end of the second receiving portion 52 remote from the first receiving portion 51 of the housing 5. The protrusions 55 contact an outer surface of the plug 31, preventing wobbling of the plug 31 during its movement. Preferably, the protrusions 55 are evenly distributed along the circumferential direction of the second receiving portion 52. A plurality of guiding portions 311 is formed on the outer surface of the bottom of the plug 31. The inner surface of the second receiving portion 52 forms guiding slots 522 corresponding to the guiding portions 311. The guiding portions 311 move in the guiding slots 522 to guide movement of the plug 31. The guiding slots 522 do not extend through the end of the second receiving portion 52 and blocking portions 524 are thus formed at ends of the guiding slots 522. The plug 31 is stopped during its outward movement by engagement between the guiding portions 311 and the blocking portions 524.

Figure 6:
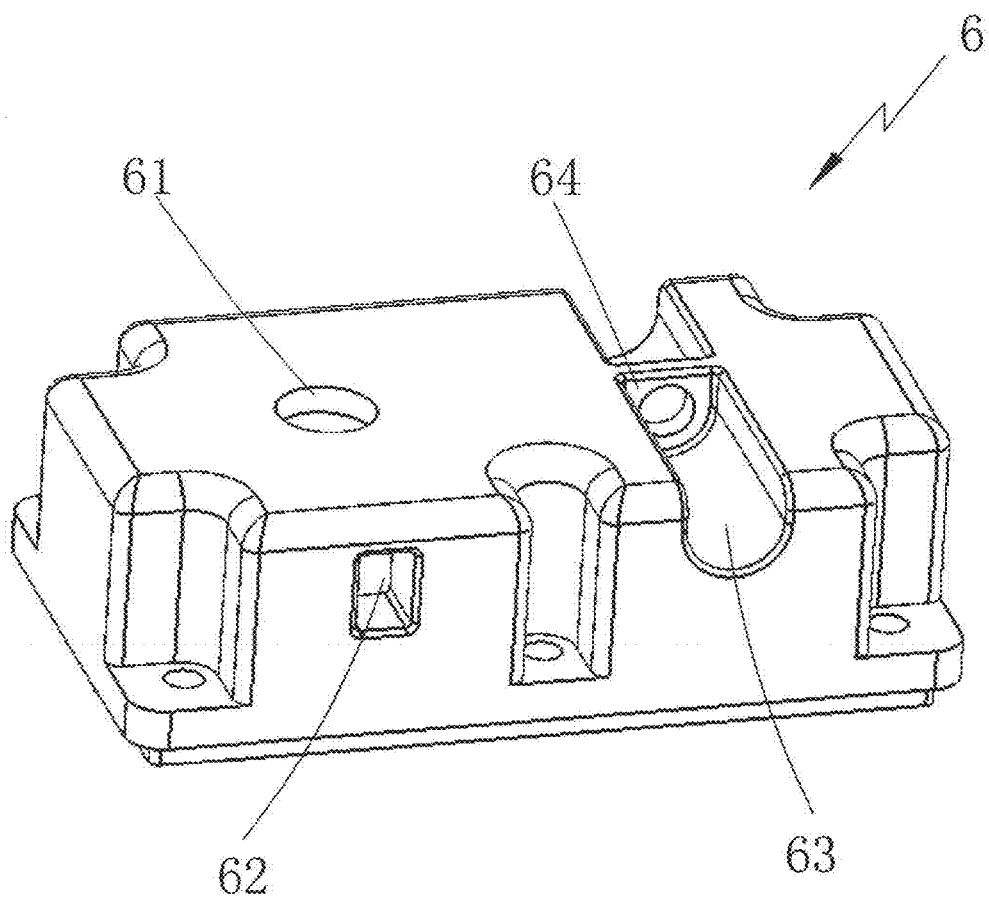
FIG. 6 illustrates a gear cover of the drive mechanism of FIG. 1.

Referring to FIG. 6, a bottom of the gear cover 6 forms a second through hole 61 corresponding to the screw shaft 32. A recess 62 is formed in a side of the gear cover 6 adjacent the second through hole 61. When this drive mechanism is mounted with an external device, a mounting pin of the external device may be mounted in the recess 62 to share the load on the housing 5 and gear cover 6, thus enabling the housing 5 and gear cover 6 to undertake a greater load. A groove 63 is formed in an outer surface of the bottom of the gear cover 6. The groove 63 extends through two opposite sides of the gear cover 6. An annular connecting portion 64 is perpendicularly disposed within the groove 63, which facilities connection of the drive mechanism with an external device.

The sensor system 4 includes a linear sensor disposed in the helical transmission system 3 and a plurality of rotation sensors disposed in the gear transmission system 2.

Figure 7:
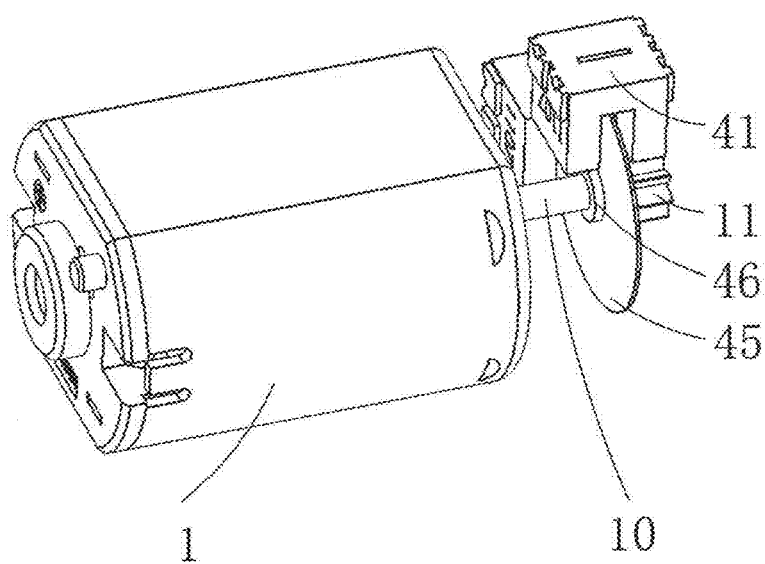
FIG. 7 to FIG. 10 illustrate a sensor system of the drive mechanism of FIG. 1.

Specifically, as shown in FIG. 7, an encoder disc 45 is disposed on the output shaft 10 of the motor 1 adjacent an inner side of the first gear 11. The encoder disc 45 is mounted to the output shaft 10 via a second collar 46. A rotation sensor 41 is mounted to the interior of the housing 5, and is disposed over the encoder disc 45. Specifically, the rotation sensor 41 is a photo sensor including a light emitter and a light receiver located at opposite sides of the encoder disc 45. The rotation sensor 41 and the encoder disc 45 cooperate to detect rotational speed and position of the output shaft 10 of the motor.

Figure 8:
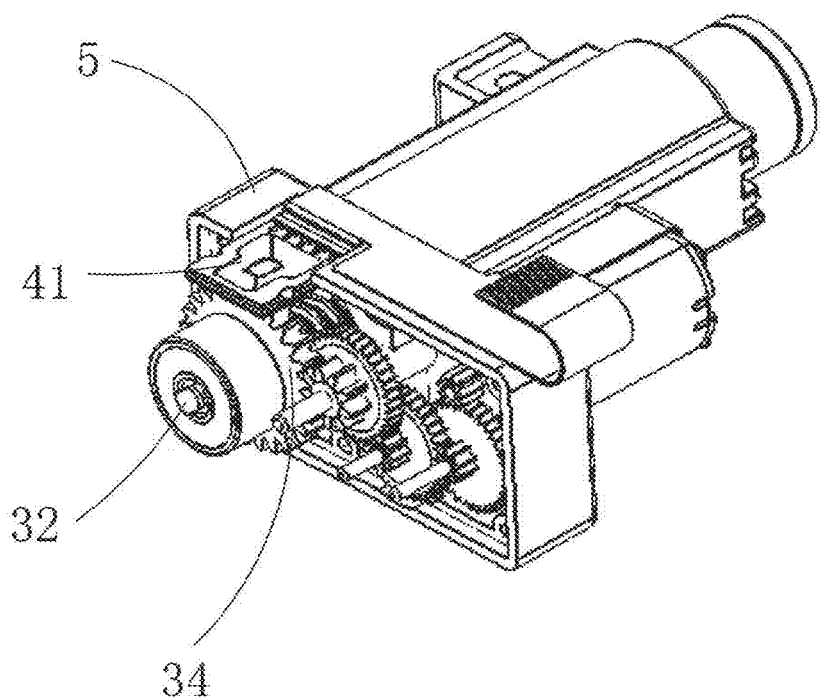

Alternatively, as shown in FIG. 8, the rotation sensor 41 may be mounted in the interior of the housing 5 adjacent the second gear 34 to directly detect the rotational speed of the second gear 34.

Figure 9:
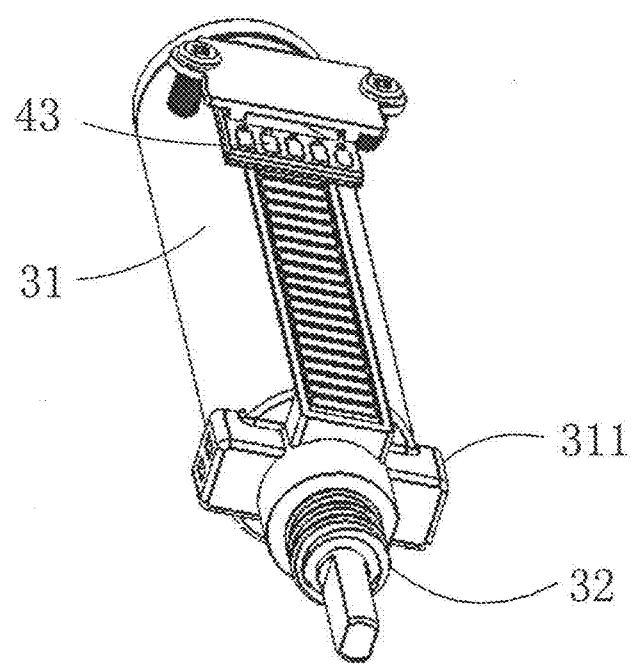
Figure 10:
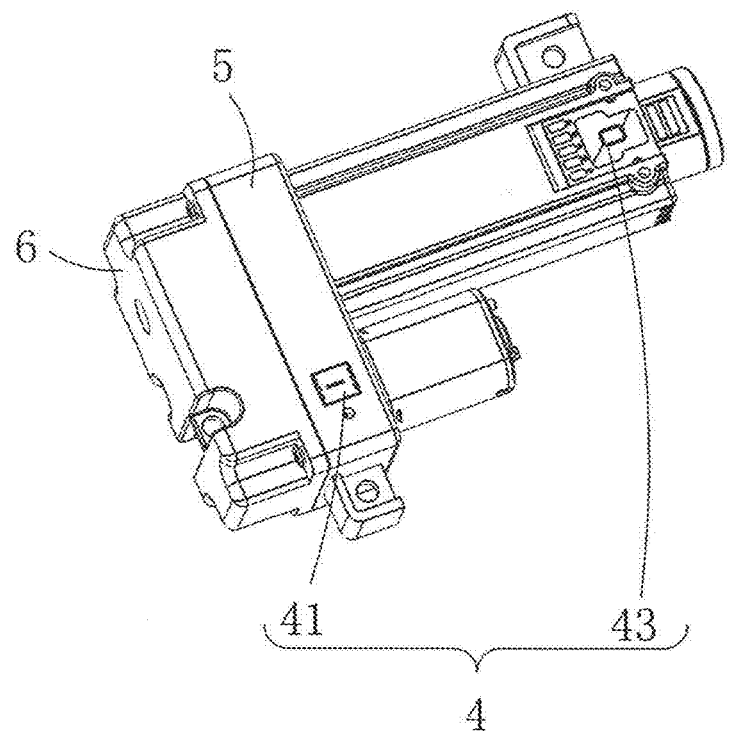
Figure 11:
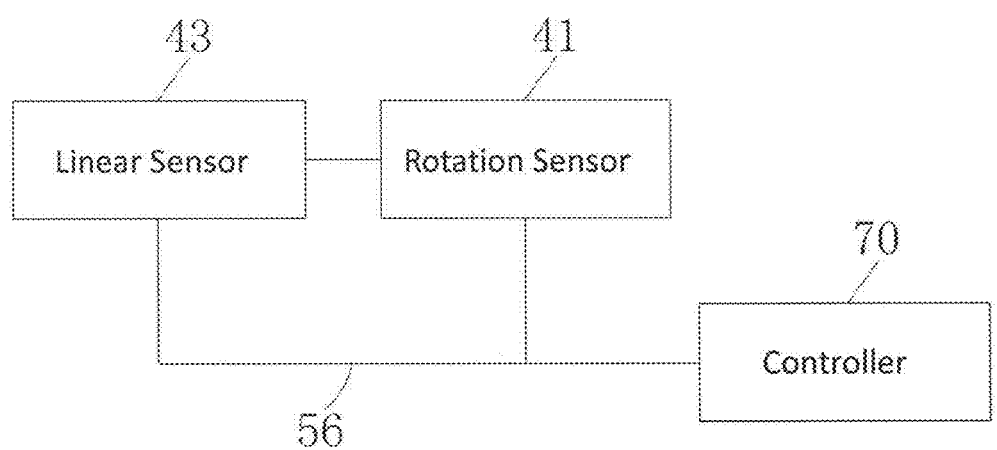
FIG. 11 is a block diagram of the sensor system and a controller of the drive mechanism of FIG. 1.

As shown in FIG. 9, a linear sensor 43 is disposed on the outer surface of the plug 31. The rotation sensor 41 monitors the rotational speed of the motor 1 or screw shaft 32. The linear sensor 43 monitors the position of the plug 31 in the helical transmission system 3.

A flexible circuit board 56 is disposed on the outer surface of the housing 5. The flexible circuit board 56 includes a flexible circuit board main body 560, a first extension portion 561 and a second extension portion 562. The first extension portion 561 lays on the outer surface of the second receiving portion 52 of the housing 5 and is electrically connected to the linear sensor 43. The second extension portion 562 is attached to an end face of the motor 1 and is electrically connected to the rotation sensor 41 at the end of the motor. The flexible circuit board 56 is electrically connected to a controller 70 to transmit the signals detected by the sensors to the controller 70. The controller 70 calculates the travel distance of the plug 31 and determines whether the travel distance of the plug 31 calculated based on the signals from the rotation sensor 41 is consistent with the travel distance of the plug 31 calculated based on the signals from the linear sensor 31. If they are inconsistent, it indicates that the drive mechanism may have a problem. If they are consistent, it indicates that the drive mechanism operates normally. Preferably, the flexible circuit board 56 is positioned by a first shielding tab 71 and a second shielding tab 72 that are mounted on the housing 5 with screws. The first shielding tab 71 and the second shielding tab 72 cover the rotation sensor 41 and the linear sensor 43, respectively.

Figure 12:
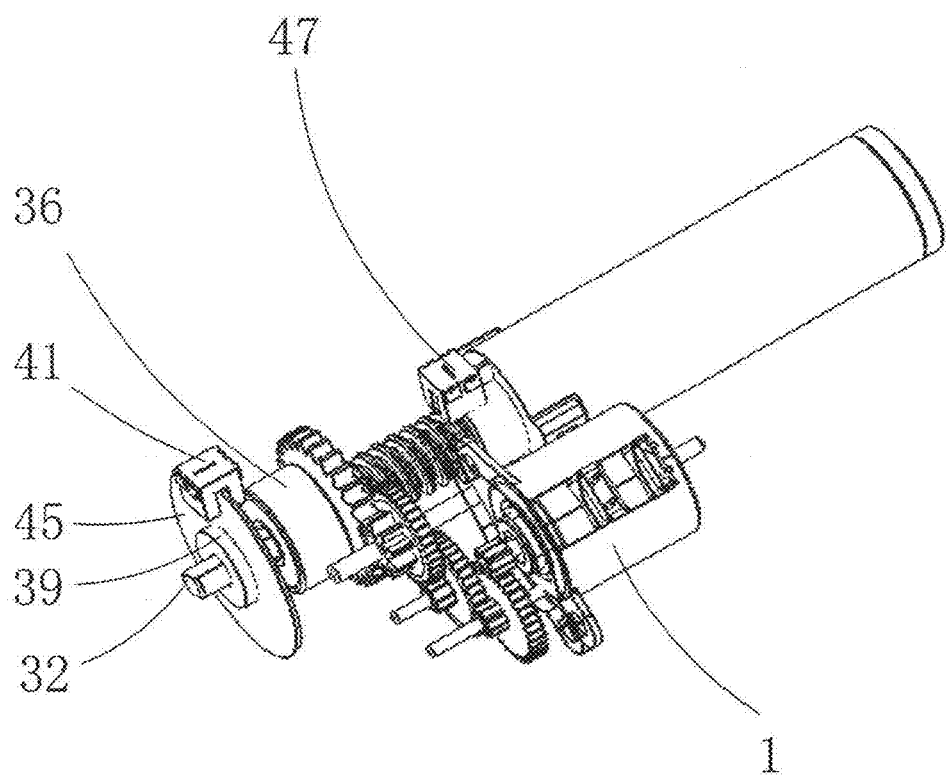
FIG. 12 is a perspective view of a drive mechanism for a medication delivery device according to another embodiment of the present invention.

Referring to FIG. 12, it should be noted that the motor 1 may also be a stepping motor. A third collar 39 may also be disposed around the screw shaft 32 adjacent the ball bearing 36, the encoder disc 45 is mounted on the collar 39, and the rotation sensor 41 is disposed over the encoder disc 45. Because a stepping motor is used, the linear sensor used in the previous embodiments may be omitted. Instead, only a reset-detecting sensor 47 is needed for detecting the plug 31 returning to its original position when the system starts up.

In summary, embodiments of the present invention provide a drive mechanism for a medication delivery device, which is capable of precise dosing of various viscous medications. Certain embodiments may have a compact construction, low noise and low power consumption. Operation of the drive mechanism may be monitored by the sensor system.

In the description and claims of the present application, each of the verbs "comprise", "include", "contain" and "have", and variations thereof, are used in an inclusive sense, to specify the presence of the stated item or feature but do not preclude the presence of additional items or features.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

The embodiments described above are provided by way of example only, and various other modifications will be apparent to persons skilled in the field without departing from the scope of the invention as defined by the appended claims.

The invention claimed is:

1. A drive mechanism for a medication delivery device, comprising a motor, a housing, a gear cover connected to the housing, a gear transmission system disposed in a space defined by the housing and the gear cover, a helical transmission system disposed in an interior of the housing and connected to the motor by the gear transmission system, and a sensor system,
wherein the helical transmission system comprises a plug, a screw shaft disposed in an interior of the plug, and a sliding block threadingly connected with the screw shaft, the sliding block being attached to or integrally formed with the plug;
wherein the motor is configured to rotate the screw shaft of the helical transmission system via the gear transmission system, to thereby move the plug along a linear path relative to the housing;
wherein the sensor system is configured to monitor a driving process of the drive mechanism; and
wherein the housing comprises a first receiving portion for receiving the gear transmission system, and a second receiving portion, perpendicular to the first receiving portion, for receiving the plug; the first receiving portion defines an opening at a side remote from the second receiving portion and has an internal space in communication with an internal space of the second receiving portion; the gear cover is mounted to the first receiving portion; a first through hole is defined in an outer surface of the first receiving portion at a location adjacent the second receiving portion, the motor is perpendicularly disposed on the outer surface of the first receiving portion, with its output shaft passing through the first through hole, the gear transmission system is disposed within the first receiving portion and the gear cover, and the helical transmission system is disposed within the second receiving portion.

2. The drive mechanism of claim 1, wherein a connecting portion is formed at an end of each of the first receiving portion and the second receiving portion.

3. The drive mechanism of claim 1, wherein the gear transmission system comprises a first gear disposed on the output shaft of the motor and a second gear disposed on one end of the screw shaft adjacent the gear cover; a ball bearing is disposed at a side of the second gear adjacent the gear cover, a first collar is disposed between the ball bearing and the second gear, an annular baffle plate is disposed at a side of the second gear remote from the gear cover, the baffle plate is mounted to an inner surface of the first receiving portion of the housing, and the baffle plate is coaxial with the second gear.

4. The drive mechanism of claim 1, wherein a plurality of protrusions is formed on an inner circumferential surface of one end of the second receiving portion remote from the first receiving portion of the housing, and the protrusions contact an outer surface of the plug.

5. The drive mechanism of claim 1, wherein a second through hole is formed in a face of the gear cover at a location corresponding to the screw shaft, a recess is formed in a side of the gear cover adjacent the second through hole, a groove is formed in an outer surface of the face of the gear cover, the groove extends through two opposite end surfaces of the gear cover, and an annular connecting portion is perpendicularly disposed within the groove.

6. The drive mechanism of claim 1, wherein the motor is a stepping motor, the sensor system comprises a reset-detecting sensor disposed in the helical transmission system and a rotation sensor disposed in the gear transmission system or adjacent the output shaft of the motor.

7. The drive mechanism of claim 1, further comprising a stop to limit over-retraction of the plug into the housing.

8. The drive mechanism of claim 1, wherein a plurality of gear shafts parallel to the output shaft of the motor is disposed in the housing, the gear transmission system comprises a first gear disposed on the output shaft of the motor, a plurality of dual gears respectively disposed on the plurality of gear shafts, and a second gear disposed on one end of the screw shaft adjacent the gear cover; the first gear meshes with a first dual gear of the plurality of dual gears adjacent the first gear, the dual gears mesh with one another, a last one of the plurality of dual gears adjacent the second gear meshes with the second gear.

9. The drive mechanism of claim 8, wherein each of the dual gears comprises a first meshing portion with a smaller diameter and a second meshing portion with a greater diameter, the first gear meshes with the second meshing portion of a first dual gear of the dual gears, the first meshing portion of the first dual gear meshes with the second meshing portion of a next stage dual gear that is immediately next to the first dual gear, the first meshing portion of the next stage dual gear meshes with the second meshing portion of a further next stage dual gear that is immediately next to the next stage dual gear, and the first meshing portion of the last stage dual gear meshes with the second gear.

10. The drive mechanism of claim 1, wherein a guiding portion is formed on one of the second receiving portion of the housing and the plug, a guiding slot is formed in the other of the second receiving portion of the housing and the plug, and the guiding portion is movable in the guiding slot to guide movement of the plug.

11. The drive mechanism of claim 10, wherein a blocking portion is formed at an end of the guiding slot to limit outward movement of the plug.

12. The drive mechanism of claim 1, wherein the sensor system comprises a linear sensor disposed in the helical transmission system and a rotation sensor disposed in the gear transmission system or adjacent the output shaft of the motor.

13. The drive mechanism of claim 12, wherein an encoder disc is disposed on the output shaft of the motor adjacent an inner side of a first gear disposed on the output shaft of the motor, the encoder disc is mounted to the output shaft via a second collar, the rotation sensor is mounted to the interior of the housing and disposed over the encoder disc, and the linear sensor is disposed on an outer surface of the plug.

14. The drive mechanism of claim 12, wherein a flexible circuit board is disposed on the outer surface of the housing, the flexible circuit board includes a flexible circuit board main body, a first extension portion and a second extension portion; the first extension portion lays on the outer surface of the second receiving portion of the housing and is electrically connected to the linear sensor, the second extension portion is attached to an end face of the motor and is electrically connected to the rotation sensor, the flexible circuit board is electrically connected to a controller.

* * * * *